US012339655B2

(12) United States Patent
Akutsu et al.

(10) Patent No.: US 12,339,655 B2
(45) Date of Patent: Jun. 24, 2025

(54) AUTOMATIC ANALYSIS DEVICE AND MAINTENANCE GUIDE METHOD IN AUTOMATIC ANALYSIS DEVICE

(71) Applicant: HITACHI HIGH-TECH CORPORATION, Tokyo (JP)

(72) Inventors: Masashi Akutsu, Tokyo (JP); Satoshi Yokotsuka, Tokyo (JP); Hiroyuki Mishima, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 482 days.

(21) Appl. No.: 17/435,379

(22) PCT Filed: Mar. 4, 2020

(86) PCT No.: PCT/JP2020/009023
§ 371 (c)(1),
(2) Date: Aug. 31, 2021

(87) PCT Pub. No.: WO2020/217720
PCT Pub. Date: Oct. 29, 2020

(65) Prior Publication Data
US 2022/0147038 A1        May 12, 2022

(30) Foreign Application Priority Data
Apr. 24, 2019    (JP) ................. 2019-082533

(51) Int. Cl.
*G05B 23/02*        (2006.01)
*G06F 3/14*         (2006.01)

(52) U.S. Cl.
CPC ..... *G05B 23/0283* (2013.01); *G05B 23/0272* (2013.01); *G06F 3/14* (2013.01)

(58) Field of Classification Search
CPC ... G05B 23/0283; G05B 23/0272; G06F 3/14; G01N 2035/009; G01N 35/00871;
(Continued)

(56) References Cited

U.S. PATENT DOCUMENTS

2005/0013736 A1*  1/2005  Mckeever ............ G01N 35/025
                                                                                  422/65
2005/0175506 A1*  8/2005  Matsubara ....... G01N 35/00712
                                                                                  422/68.1
(Continued)

FOREIGN PATENT DOCUMENTS

| JP | H10-38889 A | 2/1998 |
|---|---|---|
| JP | 2004-028932 A | 1/2004 |
| JP | 2007-316092 A | 12/2007 |

OTHER PUBLICATIONS

Takazou Fujita, "Analyzer" (espacenet machine translation of Japanese Application JP2008051542A), Aug. 22, 2006, espacenet machine translation (Year: 2006).*

(Continued)

*Primary Examiner* — Christopher W Carter
(74) *Attorney, Agent, or Firm* — Baker Botts L.L.P.

(57) ABSTRACT

Provided are an automatic analysis apparatus in which plurality of units are connected and which can perform maintenance on any unit in parallel, and a maintenance guide method for the automatic analysis apparatus. The control unit 114 causes a display unit 116 to display a maintenance guide screen 201 in which maintenance guidance (a display region for sampler module 231, a display region for second analysis module 230, and a display region for first analysis module 232) independent of analysis modules 107, 207 and a sampler module 200 is arranged in the same screen.

12 Claims, 8 Drawing Sheets

(58) Field of Classification Search
CPC ............. G01N 35/00623; G01N 35/02; G01N 2035/0091; G16H 10/40; G16H 40/40
See application file for complete search history.

(56) References Cited

U.S. PATENT DOCUMENTS

| | | | | |
|---|---|---|---|---|
| 2012/0109529 A1* | 5/2012 | Ariyoshi | ............... | G01N 35/026 702/19 |
| 2013/0274617 A1* | 10/2013 | Hosaka | ................. | A61B 5/082 702/85 |
| 2013/0311243 A1* | 11/2013 | Taki | ................ | G01N 35/00623 705/7.38 |
| 2014/0119994 A1* | 5/2014 | Ariyoshi | ................ | G01N 33/50 422/68.1 |
| 2015/0260742 A1* | 9/2015 | Nakajima | ........ | G01N 35/00613 422/63 |
| 2015/0293134 A1* | 10/2015 | Matsumoto | ...... | G01N 35/00623 422/67 |
| 2016/0092638 A1* | 3/2016 | Padmani | ................ | G16H 70/40 705/2 |
| 2018/0224477 A1* | 8/2018 | Noda | ................. | G01N 35/1004 |

OTHER PUBLICATIONS

International Search Report, mailed Jun. 2, 2020, for International Application No. PCT/JP2020/009023.
Extended European Search Report, mailed Dec. 6, 2022, for European Application No. 20795311.8.

* cited by examiner

MAINTENANCE SCREEN 301

| No. | MAINTENANCE CLASSIFICATION |
|---|---|
| 1 | USER MAINTENANCE |
| 2 | CHECK |
| 3 | |
| 4 | SERVICE MAINTENANCE |
| 5 | REGULAR MAINTENANCE |
| 6 | |
| 7 | |
| 8 | |
| 9 | |
| 10 | PRELIMINARY MAINTENANCE |

305  306  302

| No. | E | S | C | ACTION | DATE |
|---|---|---|---|---|---|
| 1 | ● | | ● | RESET | 18/12/2018 |
| 2 | ● | ● | ● | MEASURE CELL BLANK | 14/12/2018 |
| 3 | | ● | ● | EXCHANGE THERMOSTATIC WATER | 14/01/2019 |
| 4 | ● | | | CLEAN REAGENT PROBE | |
| 5 | | | ● | CLEAN FLOW PATH | 02/01/2019 |
| 6 | | | ● | CLEAN THERMOSTATIC TANK | 26/11/2018 |
| 7 | | | ● | REPLACE REACTION CELL | 23/11/2018 |
| 8 | | | ● | PERFORM OPTICAL SYSTEM MAINTENANCE | |
| 9 | ● | | ● | CLEAN SYSTEM | 14/01/2019 |
| 10 | | | ● | CLEAN SAMPLE PROBE | 20/12/2018 |

305  308  309  310  303  A

MAINTENANCE GUIDE  614

Close  615

AUTOMATIC ANALYSIS DEVICE AND MAINTENANCE GUIDE METHOD IN AUTOMATIC ANALYSIS DEVICE

TECHNICAL FIELD

The present invention relates to an automatic analysis apparatus that performs quantitative and qualitative analysis of a biological sample (hereinafter referred to as a specimen or sample) such as blood, plasma, serum, urine, and other body fluids, and a maintenance guide method in the automatic analysis apparatus, and particularly to the automatic analysis apparatus including a plurality of analysis units and a maintenance guide method thereof.

BACKGROUND ART

As an example of an automatic analysis apparatus that displays necessary preparations prior to an operation for analysis in the automatic analysis apparatus and allows an operator who is unfamiliar with the operation of the apparatus to execute all necessary preparations in advance, an automatic analysis apparatus is described, in JP-A-2004-028932 (PTL 1), in which the operator is made aware of necessary preparations before analysis by changing a display color of a maintenance button, a data erasure button, a reagent status button, a reagent prime button, a calibration button, and a QC button arranged on a system overview screen displayed on an operation unit to red, yellow, and the like according to an actual status of apparatus.

CITATION LIST

Patent Literature

PTL 1: JP-A-2004-028932

SUMMARY OF INVENTION

Technical Problem

The automatic analysis apparatus that automatically performs quantitative and qualitative analysis of samples such as blood and urine has become very popular mainly in university hospitals and clinical laboratory centers where many patient samples need to be processed in a short time, and various large-sized, medium-sized, and small-sized automatic analysis apparatuses have been developed depending on their processing capability.

In particular, in the case of a large-sized analysis apparatus that performs analysis processes on a large number of samples, a sample container containing a sample is held in a holder called a sample rack and then transported to a plurality of analysis units via a transport line (transport device), and the analysis is automatically performed up to the output of the analysis result by simply putting the rack into a sample rack input port by an inspection engineer.

In recent years, the analysis units to be connected are made usable for multiple purposes, there are also a biochemistry analysis unit that measures cholesterol or the like in the blood, an immunity analysis unit that measures infectious diseases, and the like, and there is also an analysis unit in which a plurality of these different types of analysis units are connected. As a result, it has become a flow of measuring various items from measuring only a large number of samples.

In addition, since it has become possible to achieve integration in an automatic analysis apparatus, a form of connecting with the transport line, which was conventionally the mainstream for a large-sized one, has been applied to the medium-sized and small-sized automatic analysis apparatuses, and is becoming widespread in medium-sized hospitals and the like.

On the other hand, in order for the analysis apparatus to output a stable measurement result, regular maintenance is indispensable, but as an area occupied by the apparatus is reduced, the complexity of the mechanism is increasing year by year, and the maintenance mentioned above is also becoming more difficult.

In the conventional apparatus, maintenance was executed by a skilled operator by reading maintenance manuals printed on paper.

In recent years, with the rapid computerization, these manuals are also provided in electronic media. In this case, the manual is stored in an internal recording medium of the apparatus or the like, and it has been changed to the form of referring to the stored manual.

Meanwhile, with the rapid increase in the total number of inspections due to declining birthrate and aging population and diversification of inspection types, the burden on the inspection engineer is increasing, and the number of apparatuses that each inspection engineer should be in charge is increasing. For that reason, even an operator who is inexperienced in skill has been forced to deal with the problem.

Based on this background, not only the manual but also a guidance function for instructing an operation procedure is incorporated in the apparatus as described in PTL 1, and even an inexperienced operator is allowed to maintain and manage the apparatus by simply operating according to the guidance function.

For example, as a maintenance action of the automatic analysis apparatus of biochemistry, there is maintenance, called optical system maintenance, in which a plurality of maintenance items (replacement of a light source lamp, replacement of a reaction cell, cleaning of a reaction tank, and the like) are performed as a series of flows.

This maintenance generally has to go through a process of 1) turning off a light source lamp, 2) being on standby until the light source lamp cools down, 3) draining circulating water from a reaction tank, 4) cleaning the reaction tank, 5) removing a reaction cell for photometry, 6) replacing the light source lamp, and then 7) attaching a reaction cell for photometry, 8) supplying the circulating water in the reaction tank, 9) turning on the light source lamp, 10) being on standby until the light source lamp stabilizes, and 11) cleaning the reaction cell and measuring a cell blank.

In each of these steps, work assistance can be implemented by displaying actions to be taken by the operator, such as opening which cover and loosening which screw, step by step on an operation screen.

When incorporating such a guidance function into the automatic analysis apparatus, it can be imagined that it is extremely difficult to operate the guidance function in an apparatus in which a plurality of analysis units are connected as described above. The reason for this is that even in the apparatus in which the plurality of analysis units are connected, a screen of an operation unit is composed of one.

In contrast, for example, it is conceivable to provide a screen for guidance exclusively for each analysis unit. However, even in such a case, in order to proceed with each maintenance operation, it is necessary to switch and display a guide screen for a first analysis unit and a guide screen for a second analysis unit, and then confirm and perform a necessary operation.

Such switching work is very complicated for the operator. There is a concern that repeated switching will cause confusion and the work to be done at present will not be known. Furthermore, there is a concern that the possibility of occurrence of mistakes is high.

That is, when executing each maintenance, there is a problem that a status of one maintenance hinders the other maintenance action and performing the maintenance actions in parallel is difficult. As a result, there is a concern that maintenance action will take time.

In addition, although a means of providing an operation unit for each analysis unit is also conceivable, since there are a wide variety of analysis apparatuses in actual inspection rooms, such a means is impractical in the automatic analysis apparatus, which is becoming smaller and more integrated.

An object of the present invention is to provide an automatic analysis apparatus in which a plurality of units are connected and maintenance for any of the units can be performed in parallel, and a maintenance guidance method in the automatic analysis apparatus.

Solution to Problem

The present invention includes a plurality of means for solving the problems described above, and one example thereof is an automatic analysis apparatus that analyzes a sample, the automatic analysis apparatus including at least one analysis unit that analyzes the sample, a transport unit that holds a plurality of sample containers housing the samples and that supplies the sample containers to the analysis unit, a display device that displays information on maintenance of the analysis unit and maintenance of the transport unit, and a control unit that controls an operation of the analysis unit and an operation of the transport unit, and that causes the display device to display information on maintenance, in which the control unit causes the display device to display a guide screen in which maintenance guidance independent of the analysis unit and the transport unit is arranged in the same screen.

Advantageous Effects of Invention

According to the present invention, in the automatic analysis apparatus in which the plurality of units are connected, maintenance for any of the units can be performed in parallel. Problems, configurations, and effects other than those described above will be clarified by the description of the following embodiments.

DESCRIPTION OF EMBODIMENTS

An embodiment of an automatic analysis apparatus and a maintenance guide method in the automatic analysis apparatus of the present invention will be described with reference to FIGS. 1 to 8.

Figure 1:
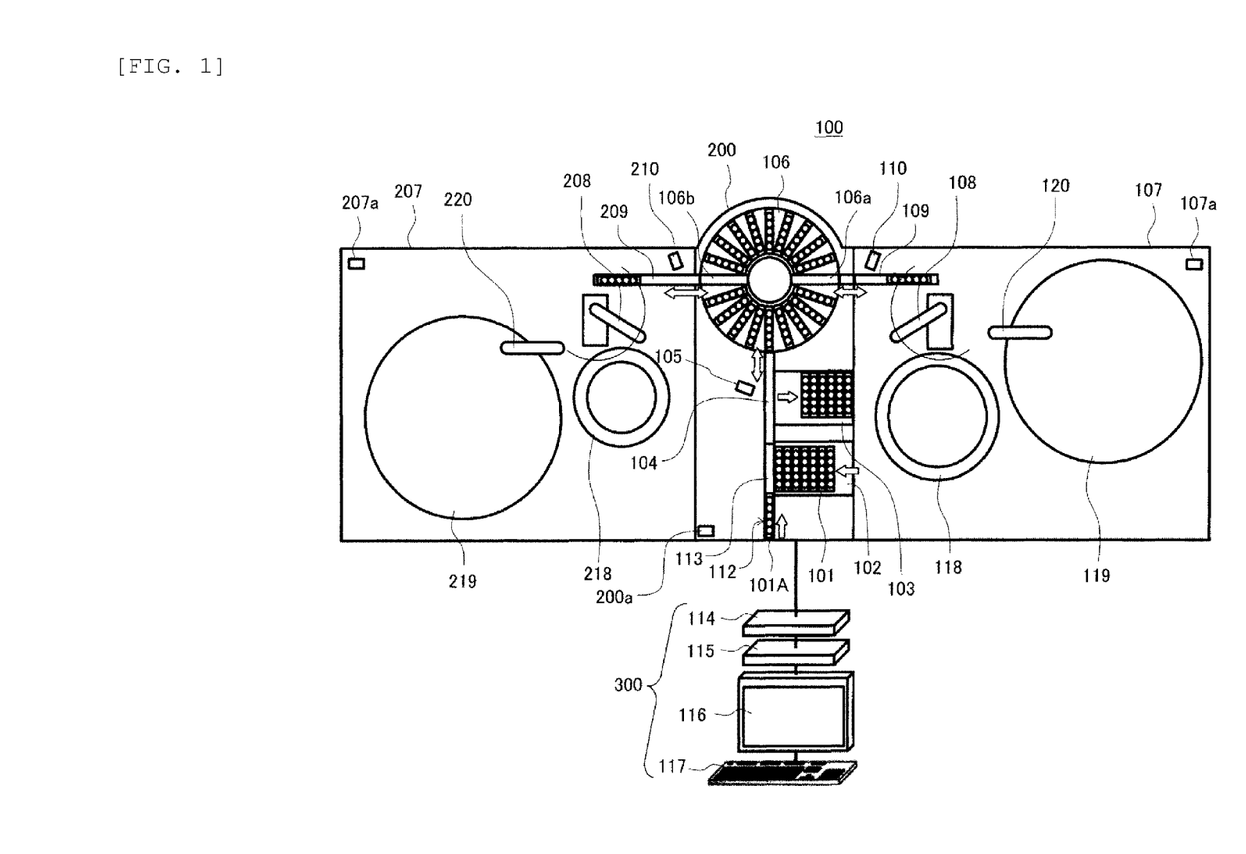
FIG. 1 is a view schematically showing an overall configuration of an automatic analysis apparatus according to a present embodiment.

First, an example of an overall configuration of the automatic analysis apparatus will be described with reference to FIG. 1. FIG. 1 is a view schematically showing an overall configuration of an automatic analysis apparatus according to a present embodiment.

In FIG. 1, an automatic analysis apparatus 100 shown as an example in the present embodiment is roughly configured with a plurality of analysis modules 107 and 207 (two in the present embodiment), a sampler module 200 for transporting a sample rack loaded with one or more sample containers containing the samples to be analyzed by the analysis modules 107 and 207, and a control device 300 that controls the overall operation of the automatic analysis apparatus 100.

Here, the sample rack is loaded with one or more sample containers in which the samples to be subjected to qualitative and quantitative analysis in the analysis modules 107 and 207 are housed.

The sample rack includes at least a sample rack (hereafter, simply referred to as sample rack 101) loaded with a sample container housing a sample (normal sample) to be analyzed with a normal priority, and a sample rack (hereinafter, referred to as an emergency sample rack 101A when distinguished from the sample rack 101) loaded with a sample container housing an emergency sample having a higher degree of urgency for analysis and measurement than the sample rack 101.

The sampler module 200 is a module that transports the sample rack 101 loaded into the automatic analysis apparatus 100 between the analysis modules 107 and 207, and includes a sample rack supply unit 102, an emergency specimen rack input unit 112, a transport line 104, and an emergency sample rack standby area 113, a sample identification device 105, a rack rotor 106, a sample rack housing unit 103, and the like.

The transport line 104 is, for example, a belt conveyor type transport mechanism that reciprocates the sample rack 101 and the emergency sample rack 101A.

The emergency specimen rack input unit 112 is provided adjacent to the transport line 104 and is a region for inputting the emergency sample rack 101A.

The sample rack supply unit 102 is provided adjacent to the transport line 104 on one end side of the transport line 104 than the emergency specimen rack input unit 112, and is a region for supplying the sample rack 101 of a normal sample.

The sample rack housing unit 103 is provided adjacent to the transport line 104 on one end side of the transport line 104 than the sample rack supply unit 102, and is a region for accommodating the sample rack 101.

The emergency sample rack standby area 113 is provided on the transport line 104 on the other end side of the transport line 104 than the sample rack housing unit 103, and is a region for making the emergency sample rack 101A temporarily stand by.

The sample identification device 105 is a mechanism for reading and identifying an identification medium (not shown) such as RFID and barcodes provided on the sample rack 101 and the sample container in order to inquire analysis request information on the sample housed in the sample container loaded on the sample rack 101 transported on the transport line 104.

The rack rotor 106 is arranged at one end of the transport line 104. The rack rotor 106 is a mechanism which includes one or more slots 106a and 106b on which the sample rack 101 and the like can be loaded and transmits and receives the sample rack 101 and the like between one end of the transport line 104 and each of one ends of dispensing lines 109 and 209 of the analysis modules 107 and 207.

For example, the rack rotor 106 has a structure that rotates clockwise and counterclockwise, and is appropriately controlled in its rotational operation so that processing is started in the order in which the sample rack 101 is input, or when the sample rack 101 having a high priority is input, the rack rotor 106 is appropriately controlled in its rotational operation so that processing can be started before the sample rack 101 inserted earlier.

The analysis modules 107 and 207 are units that perform qualitative and quantitative analysis by sampling (dispensing) the samples housed in the sample container loaded on the sample rack 101, and include dispensing lines 109 and 209, sample identification devices 110 and 210, reaction disks 118 and 218, sample dispensing mechanisms 108 and 208, reagent disks 119 and 219, and reagent dispensing mechanisms 120 and 220, measuring units (not shown) and the like, respectively.

The dispensing lines 109 and 209 adopt a transport mechanism which is capable of reciprocating operation and pulls the sample rack 101 from the sampler module 200 to the analysis modules 107 and 207 and delivers the sample rack 101 from the analysis modules 107 and 207 to the sampler module 200. For example, the transport mechanism is a belt conveyor type mechanism.

Although a case where a belt conveyor type transport mechanism is adopted as the dispensing lines 109 and 209 is illustrated, a configuration in which a protrusion structure driven along the dispensing lines 109 and 209 is fitted into a recess provided in advance in the sample rack 101 and transported can be adopted. Such a configuration is the same for the transport line 104.

The sample identification devices 110 and 210 are mechanisms which are provided adjacent to the other end side of the dispensing lines 109 and 209, and read and identify an identification medium (not shown) such as RFID and barcodes provided on the sample rack 101 and the sample container in order to collate analysis request information for the samples housed in the sample rack 101 carried into the dispensing lines 109 and 209.

The sample dispensing mechanisms 108 and 208 are mechanisms for dispensing samples from the sample containers of the sample rack 101 transported to dispensing positions on the dispensing lines 109 and 209 into reaction containers of the reaction disks 118 and 218.

The reagent dispensing mechanisms 120 and 220 are mechanisms for dispensing the reagents housed in the reagent containers of the reagent disks 119 and 219 into the reaction containers of the reaction disks 118 and 218.

The measuring unit is a mechanism for performing qualitative and quantitative analysis by measuring a mixed solution (reaction solution) of the sample and the reagent dispensed into the reaction container.

The sampler module 200 and the analysis modules 107 and 207 respectively include in-module control units 107a, 207a, and 200a each control an operation of a device in each module independently of operations of other modules. These in-module control units 107a, 207a, and 200a are configured so that each device in each module can operate based on a command signal from the control unit 114.

In the present embodiment, the analysis module 107 is assumed to be a unit for biochemistry inspection, and the analysis module 207 is assumed to be a unit for immunological inspection. In this case, the purpose and processing capability of the inspection are different.

In addition to that, a measuring unit for measuring an electrolyte concentration may be provided in the analysis module 107, or a measuring unit for blood coagulation analysis or the like may be appropriately arranged in each module according to application.

Furthermore, when the purpose (inspection item) is the same, it is possible to adopt a configuration in which the same processing capability is maintained for a plurality of analysis modules with the same analysis module, and when only the purpose is different, it is possible to adopt a configuration in which a plurality of different analysis modules are connected.

The control device 300 is a device that controls the overall operation of the automatic analysis apparatus 100 including the devices of the analysis modules 107 and 207 and the sampler module 200, and is a computer provided with a CPU, a memory, and the like.

The control device 300 is configured with a display unit 116, an input unit 117, a storage unit 115, a control unit 114, and the like.

The display unit 116 is a display device such as a liquid crystal display that displays an input screen for various parameters and settings, and information such as analytical inspection data for initial inspection or re-inspection, measurement results, and displays information related to maintenance of the analysis modules 107 and 207 and the sampler module 200. The display unit may be configured with a touch panel type display device that also serves as the input unit 117, which will be described later.

The input unit 117 is configured with a keyboard and a mouse for inputting various data such as various parameters and settings, analysis request information, and instructions for starting analysis.

The storage unit 115 is a recording medium such as a semiconductor memory such as a flash memory or a magnetic disk such as an HDD that records the measurement result of the sample input into the automatic analysis apparatus 100 and the analysis request information of the sample housed in the sample container loaded on each sample rack. The storage unit 115 also records various parameters and set values for controlling the operation of each device in the automatic analysis apparatus 100, various computer programs for performing various display processes described later, and the like.

The control unit 114 is a part that controls the overall operation of the automatic analysis apparatus 100 including the control device 300, and is the CPU described above and the like.

In the present embodiment, the control unit 114 performs control for displaying a screen, on which various information such as information on the sample, information on an analysis item, and information on an analysis result are displayed, on a display screen of the display unit 116. Furthermore, the control unit performs control for displaying various screens related to the operation of the automatic analysis apparatus 100, such as an operation screen for starting analysis, an analysis progress status, a screen for instructing to perform maintenance, information on maintenance progress status, a maintenance guide screen, and the like. The details will be described later with reference to each figure.

The matters described above are a general configuration of the automatic analysis apparatus 100.

The analysis process of the sample by the automatic analysis apparatus 100 as described above is generally performed in the following order.

The operator gives an analysis instruction to the automatic analysis apparatus 100 using the display unit 116 and the input unit 117. The analysis instruction is stored in the storage unit 115 and transmitted to a target analysis module among the sampler module 200 and the analysis modules 107 and 207 via the control device 300. The target module performs an analysis operation as follows according to the received analysis instruction.

The sampler module 200 sends the sample racks 101 installed in the sample rack supply unit 102 one by one onto the transport line 104 and carries them into the rack rotor 106.

The sample rack 101 transported to the rack rotor 106 is transported to the dispensing line 109 of the analysis module 107 or the dispensing line 209 of the analysis module 207 depending on a measurement item requested by the control device 300.

When the sample rack 101 arrives at the dispensing line 109 or 209, a dispensing operation is executed by the sample dispensing mechanism 108 or 208 for each sample loaded on the sample rack 101.

When the measurement item is a biochemistry item, the sample dispensing mechanism 108 discharges a sucked specimen into the reaction container on the reaction disk 118. After that, the reagent sucked from the reagent disk 119 by the reagent dispensing mechanism 120 is further added to the reaction container, and stirred. After that, absorbance and the like are measured by the measuring unit, and the measurement result is transmitted to the control unit 114 of the control device 300.

The reaction container used for the analysis is cleaned with water, an alkaline detergent, and an acidic detergent dispensed from a cleaning mechanism (not shown), and is used for the next analysis.

When the measurement item is an immunological item, the reagent sucked from the reagent disk 219 by the reagent dispensing mechanism 220 is discharged into the reaction container on the reaction disk 218, and a specimen is further added to the reaction container by the sample dispensing mechanism 208 and stirred. After that, processing such as magnetic separation is performed as necessary, and then the measurement is performed by the measuring unit and the measurement result is transmitted to the control unit 114 of the control device 300.

The control unit 114 obtains the concentration of a specific component in the specimen from the transmitted measurement result by arithmetic processing, and performs processing such as causing the result to be displayed on the display unit 116 or the like, or storing the result in the storage unit 115 and the like.

Next, the details of maintenance in the automatic analysis apparatus 100 of the present embodiment will be described with reference to FIG. 2 and subsequent figures.

First, the display screen and the like during maintenance will be described with reference to FIGS. 2 to 6.

Figure 2:
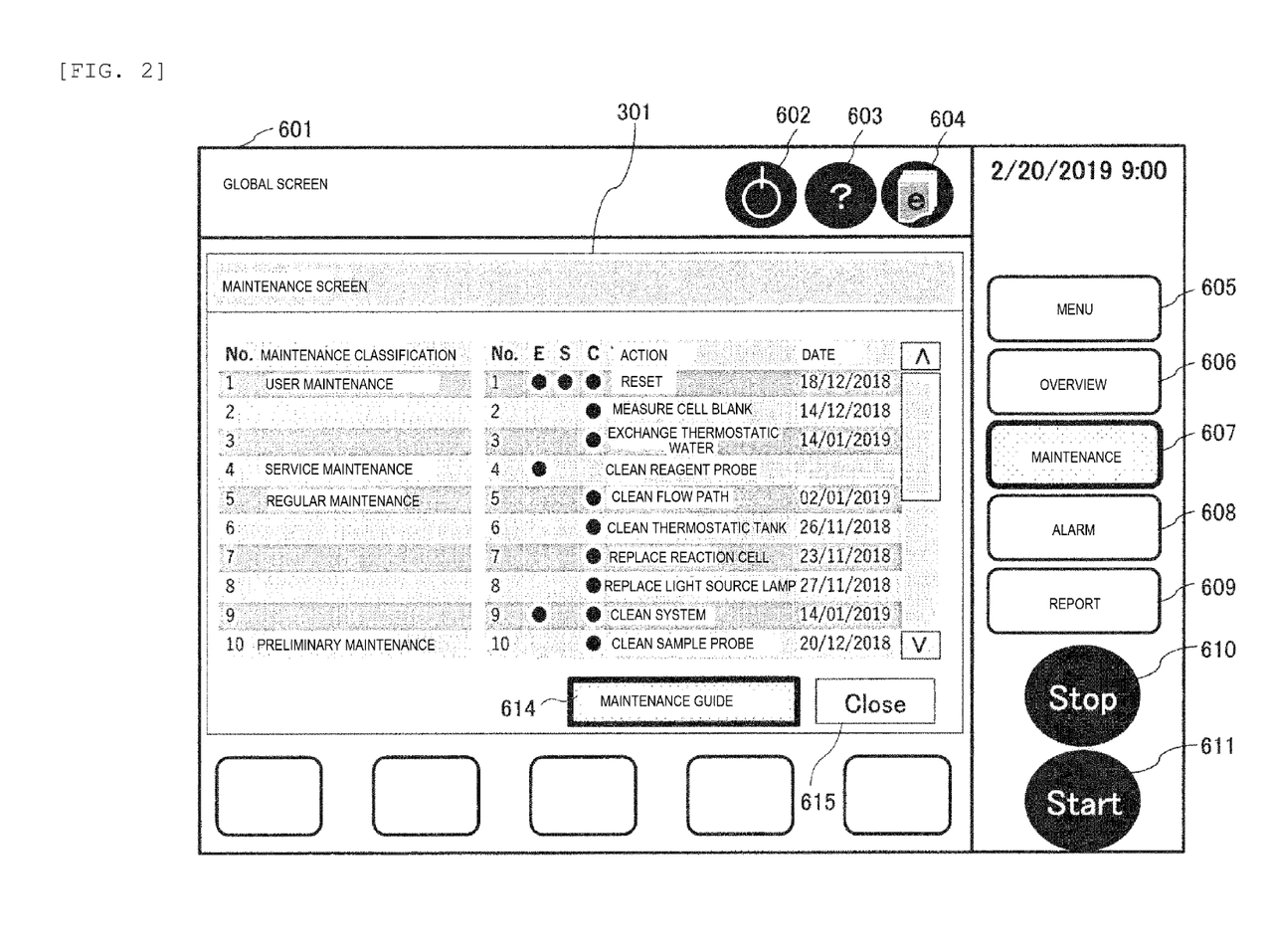
FIG. 2 is a diagram showing an outline of a global screen and a display that recommends a transition from the global screen to a maintenance screen according to the present embodiment.
Figure 3:
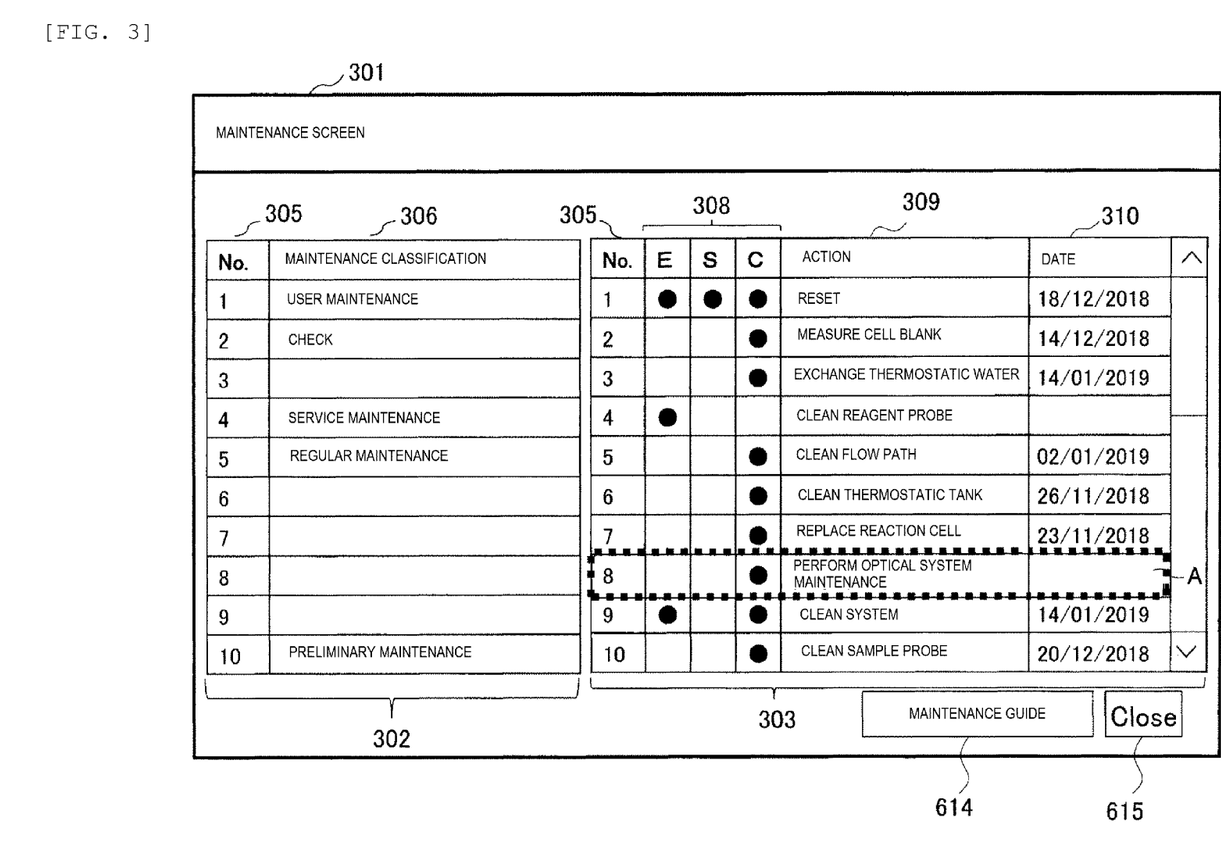
FIG. 3 is a diagram showing an outline of the maintenance screen and a transition from the maintenance screen to a maintenance guide screen according to the present embodiment.
Figure 4:
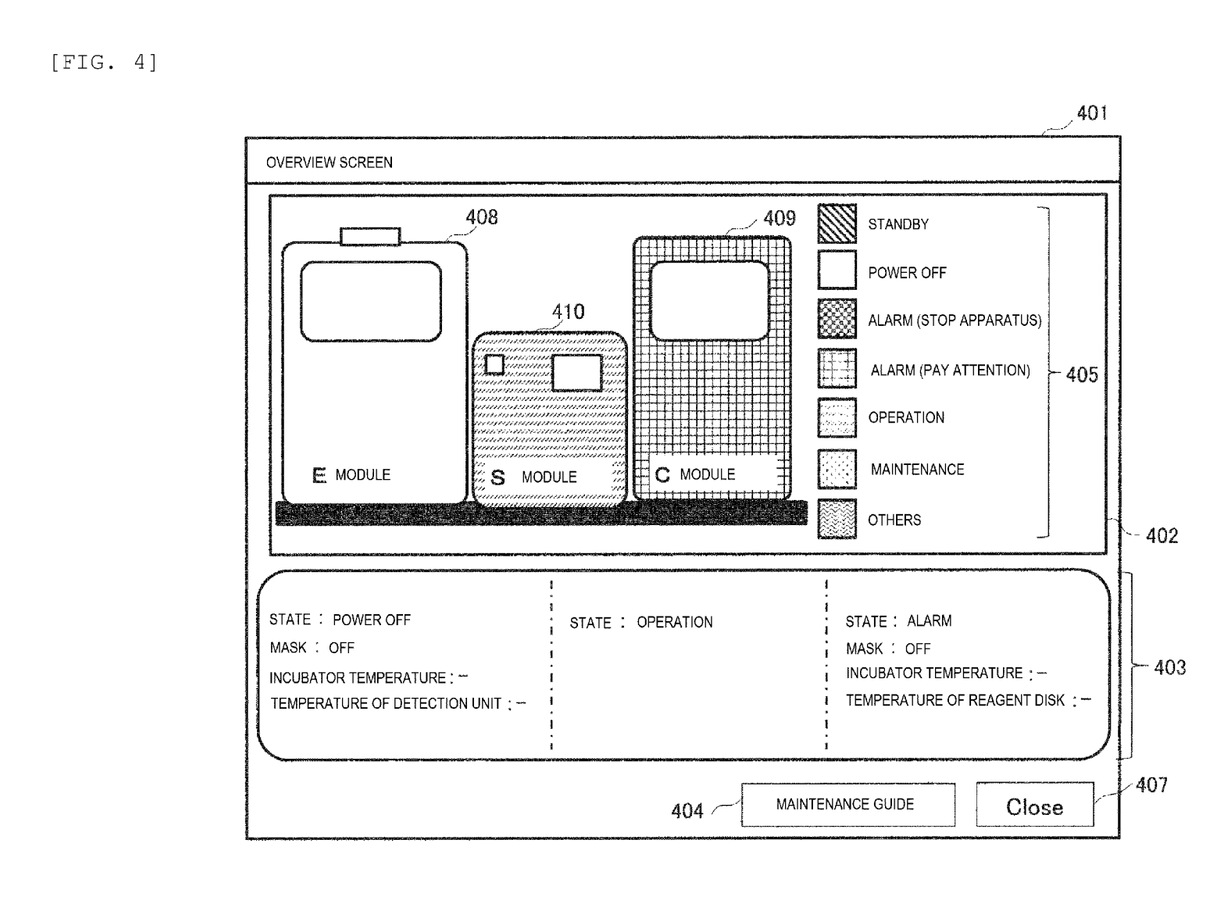
FIG. 4 is a diagram showing an outline of an overview screen and a transition from the overview screen to the maintenance guide screen according to the present embodiment.
Figure 5:
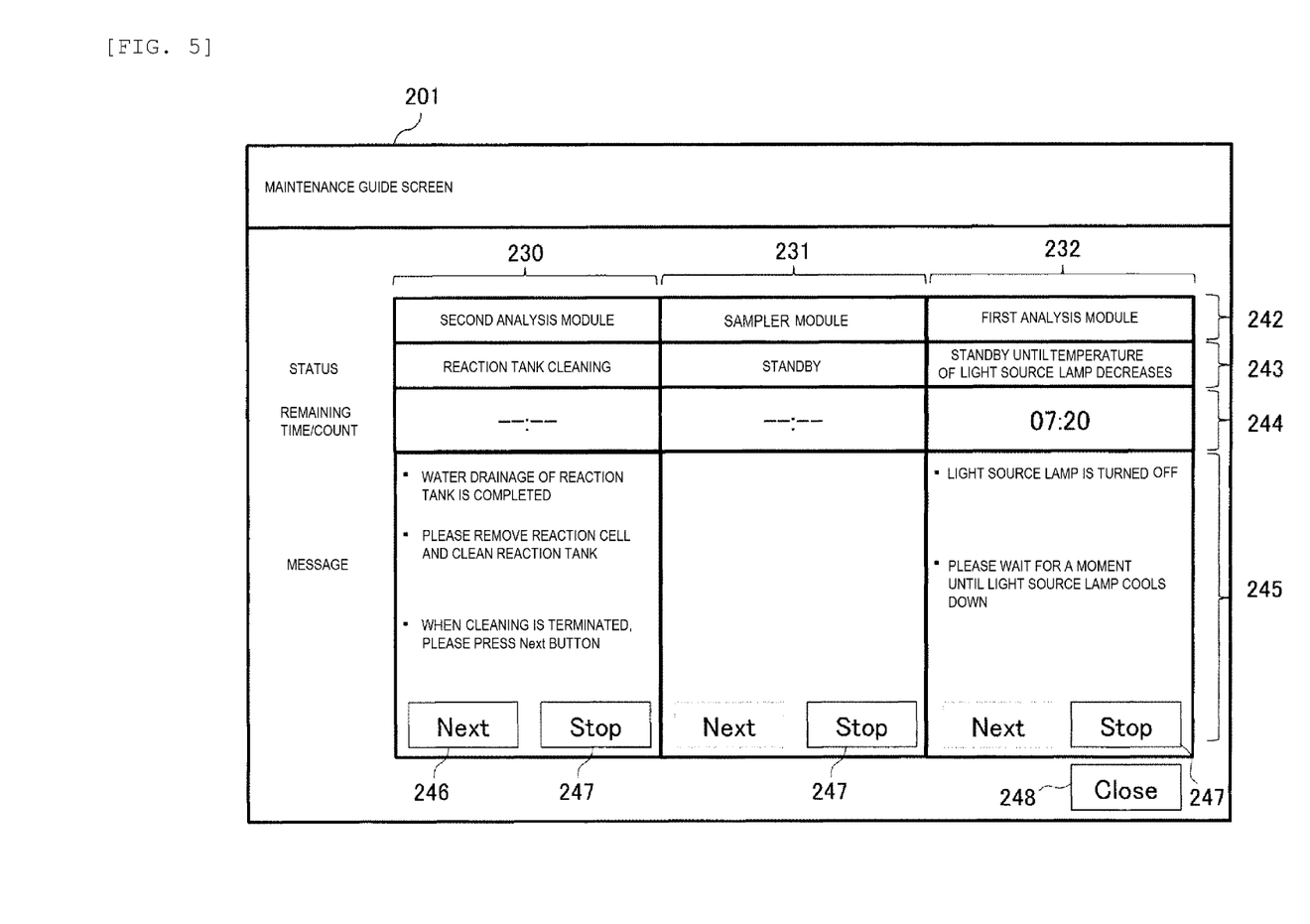
FIG. 5 is a diagram showing an example of the maintenance guide screen in the automatic analysis apparatus according to the present embodiment.
Figure 6:
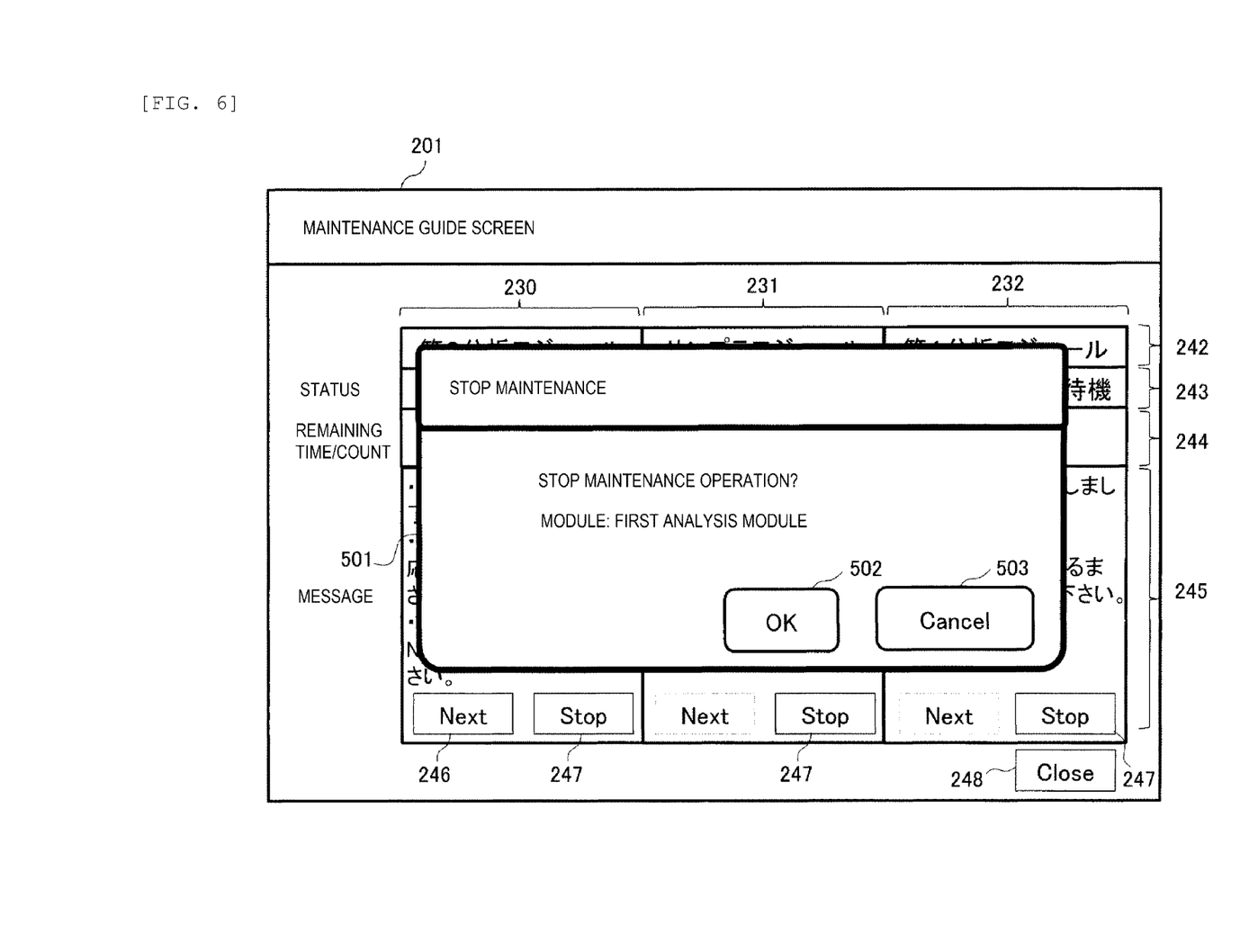
FIG. 6 is a diagram showing a confirmation screen when maintenance is stopped in the maintenance guide screen according to the present embodiment.

FIG. 2 is a diagram showing an outline of a global screen and a display that recommends a transition from the global screen to a maintenance screen. FIG. 3 is a diagram showing an outline of the maintenance screen and a transition from the maintenance screen to a maintenance guide screen. FIG. 4 is a diagram showing an outline of an overview screen and a transition from the overview screen to the maintenance guide screen. FIG. 5 is a diagram showing an example of the maintenance guide screen. FIG. 6 is a diagram showing a confirmation screen when maintenance is stopped in the maintenance guide screen.

The display control of each screen shown below is performed by the control unit 114 of the control device 300 as described above.

The global screen 601 shown in FIG. 2 is a screen displayed on the operation screen of the display unit 116 of the control device 300, and is composed of a global region that is displayed in common to all states and a local region whose contents change according to each state.

On a global screen 601 shown in FIG. 2, a power button 602, a help button 603, an online manual button 604, a menu button 605, an overview button 606, a maintenance button 607, an alarm button 608, a report button 609, a start button 611, a stop button 610, a maintenance screen 301, and the like are displayed.

In the example shown in FIG. 2, the global region on the global screen 601 corresponds to a portion other than the maintenance screen 301.

The maintenance screen 301 shown in FIG. 3, an overview screen 401 shown in FIG. 4, and a maintenance guide screen 201 shown in FIG. 5 are screens displayed in the local region of the global screen 601.

The online manual button 604 is a region for referring to an online manual. The menu button 605 is a region for displaying various menu icons.

The overview button 606 is a region for selecting display of the overview screen shown in FIG. 4, which will be described later. The maintenance button 607 is a region for selecting the display of the maintenance screen shown in FIG. 3, which will be described later.

The alarm button 608 is a region for selecting the display of the detailed contents of an alarm. The report button 609 is a region for selecting the display of various reports to an operator.

The start button 611 is a region for selecting and instructing to start the execution of a process, and the stop button 610 is a region for selecting and instructing to stop the execution of the process.

When the control unit 114 recognizes that the start button 611 has been pressed, the control unit 114 starts the analysis process. When the device is placed in a state where analysis cannot be performed, such as during maintenance or warming up, it is desirable to perform either a process of preventing the start button 611 from being pressed, or notifying the operator of the reason why the analysis cannot be performed without starting the analysis even if the start button 611 is pressed.

When the control unit 114 recognizes that the stop button 610 has been pressed, it is desirable that the control unit 114 stops an operation of the device even if the device is in any state, such as cessation of the analysis, cessation of the maintenance, and the like, but the control unit 114 may only stop the analysis.

As shown in FIGS. 2 and 3, the maintenance screen 301 is mainly composed of a maintenance classification display region 302 and a maintenance detailed information display region 303.

In the maintenance classification display region 302, for each item in the maintenance item No. 305, maintenance information classified into each category in the maintenance classification 306 is shown.

For example, "user maintenance" including maintenance such as replacement, cleaning, and reset of various parts, "check" to check an operation of each mechanism such as each dispensing mechanism and each disk, "preliminary maintenance" that manages the expiration date and the like in units of parts of each module, "service maintenance" including dedicated maintenance by a service person, "regular maintenance" including maintenance that needs to be performed regularly, such as daily, weekly, and monthly, and the like are displayed.

In the maintenance detailed information display region 303, each maintenance corresponding to the maintenance item No. 305 shown in the maintenance classification display region 302, is shown as information on each module 308 indicating which of the modules requires maintenance, action information 309 indicating actions mainly necessary for maintenance, and date and time information 310 which is information on the date and time when the maintenance was executed.

In information on each module 308 of FIG. 3, "E" indicates the analysis module 207, "S" indicates the sampler module 200, and "C" indicates the analysis module 107.

In FIG. 3, only the date information is shown as the date and time information 310, but it is also possible to display up to the time as more detailed information.

Here, the operator can instruct the start of maintenance by selecting the maintenance to be performed on the device (for example, maintenance of the optical system of No. 8 shown in the region of the dotted line A in FIG. 3) and pressing the start button 611 or the like displayed at the time of selection.

Here, in the present embodiment, the control unit 114 causes a maintenance guide button 614 for transitioning to the maintenance guide screen 201 to be displayed on the global screen 601 even when the global screen 601 is displayed on the display unit 116.

For example, on the maintenance screen 301 shown in FIG. 3, the operator confirms a performance state of maintenance of each module in an actual device, confirms necessary guidance, and selects the maintenance guide button 614 when performing the operation. With this configuration, transition to the maintenance guide screen 201 of FIG. 5, which will be described later, is possible.

When the operator is displaying a screen other than the maintenance guide screen 201, such as the maintenance screen 301 shown in FIG. 3, during performance of maintenance of each module, if the maintenance performed by the operator in the background is terminated and the operator needs to perform the next operation, it is desirable that the control unit 114 causes notification information to be displayed.

As a way of notifying the notification information, for example, a method such as displaying colors and patterns of the maintenance button 607 shown in the global region and the maintenance guide button 614 on the global screen 601 in a distinctive manner can be used. Furthermore, in addition to this aspect, it is also possible to display a pop-up or the like as a screen showing a message recommending the transition to the maintenance guide screen 201, for example.

In this case, when the displayed screen is other than the maintenance screen 301, for example, when it is a screen for ordering analysis and the like, the operator first presses the maintenance button 607 in the global region to make the screen transition to the maintenance screen 301 shown in FIG. 3. After that, it is possible to make transition to the maintenance guide screen 201 by pressing the maintenance guide button 614 to confirm the necessary operation.

Although the case where the maintenance guide button 614 for making transition to the maintenance guide screen 201 is displayed in the local region where the maintenance screen 301 is displayed as shown in FIG. 2 has been described, the maintenance guide button 614 can be displayed in the global region. For example, it can be displayed between the maintenance button 607 and the alarm button 608 or the like.

It is possible to return to the previous screen by selecting the Close button 615.

The overview screen 401 shown in FIG. 4 is a screen for grasping an outline of the performance state of maintenance, and as shown in FIG. 4, is mainly composed of a layout display region 402 and a status display region 403.

In the layout display region 402, the respective modules are shown in the same layout as the actual arrangement. In FIG. 4, "E module (immunity) 408" indicates the analysis module 207, "S module 410" indicates the sampler module 200, and "C module (biochemistry) 409" indicates the analysis module 107.

In the layout display region 402, the status of each module is displayed so that it is possible to visually recognize what status each module is in by each pattern shown in the detailed information display region 405 or by classification such as color coding.

The status display region 403 shows more detailed information of each of the modules.

When the overview screen 401 is displayed, the operator confirms the performance status of maintenance of each module in the actual device, and selects the maintenance guide button 404 when confirming the necessary guidance and performing the operation, thereby capable of making transition to the screen of FIG. 5 described later.

It is possible to return to the previous screen by selecting the Close button 407.

Next, the maintenance guide screen in the automatic analysis apparatus according to the present embodiment will be described with reference to FIG. 5.

The maintenance guide screen 201 shown in FIG. 5 is a screen displayed on the operation screen of the display unit 116 of the control device 300. As shown in FIG. 5, the maintenance guide screen 201 is composed of a display region for sampler module 231, a display region for second analysis module 230, a display region for first analysis module 232, and a Close button 248.

The display region for sampler module 231 shown in FIG. 5 is a region for displaying maintenance guidance of the sampler module 200, the display region for second analysis module 230 is a region for displaying maintenance guidance of the analysis module 207, and the display region for first analysis module 232 is a region for displaying maintenance guidance of the analysis module 107.

As shown in FIG. 5, in the maintenance guide screen 201, the display region for sampler module 231, the display region for second analysis module 230, and the display region for first analysis module 232 are arranged in the same screen.

In the maintenance guide screen 201, the display region for sampler module 231, the display region for second analysis module 230, and the display region for first analysis module 232 are displayed in the same arrangement as that (actual device layout) of each unit when the automatic analysis apparatus 100 is viewed from a position where the operator views the maintenance guide screen 201.

In each of the display regions for the modules, a module name display region 242, a status display region 243, a remaining time/count information display region 244, a guidance information display region 245, a Next button 246, and a Stop button 247 are displayed.

In the module name display region 242, a unique name that can identify each module is displayed.

In the status display region 243, the status of the device of the corresponding module (device state) is displayed.

In the remaining time/count information display region 244, the remaining time of the maintenance operation of each corresponding module or the number of times of operation count in the check function for performing repetitive operations is displayed. FIG. 5 shows, as an example, an example in which remaining time information is displayed in the remaining time/count information display region 244.

The case where the remaining time is displayed in the remaining time/count information display region 244 is desirably a case where the maintenance operation having a fixed time until the termination is being performed or a case where the number of times of repetition and the operation of each time are fixed and the operation having a predetermined time until the termination is performed.

The case of displaying the number of times of operation is desirably a case in which the termination time of the maintenance operation is not determined. For example, this is the case when an operation for which the time until the termination of maintenance is not determined in advance is being performed, such as a case when the number of times of operation is not fixed and it is performed 100 times at a certain timing A and 10 times at a certain timing B, or a case when the time for each operation is not fixed.

In the guidance information display region 245, guidance to be provided to the operator for the maintenance operation of the corresponding module is displayed.

The Next button 246 is a selection region for making a transition to the next step for the maintenance operation of the corresponding module. The Stop button 247 is a selection region for interrupting the maintenance operation for the maintenance operation of the corresponding module.

It is desirable that the Stop button 247 can be pressed when a situation under which the maintenance operation has to be interrupted occurs during each maintenance. It is desirable that the Stop button 247 is always valid during the maintenance execution period, and that the maintenance can be interrupted if the button is pressed.

For example, in the maintenance guide screen 201 shown in FIG. 5, when the Stop button 247 is selected by the operator when the maintenance for a specific module is stopped, a confirmation screen 501 shown in FIG. 6 is displayed as a pop-up.

The confirmation screen 501 shows a message confirming whether or not maintenance may be stopped, and indicates which module the instruction is for.

After confirming the confirmation screen 501, the operator can select an OK button 502 when he or she wants to continue the stop, and can select the Cancel button 503 when he or she wants to cancel the stop. With this configuration, it is possible to prevent the operator from instructing an unintended module to stop maintenance due to an operation error or the like.

Meanwhile, it is desirable that the Next button 246 is configured to be enabled (can be pressed) only in a situation under which the necessary operation is completed and it is possible to proceed to the next step. With this configuration, it is possible to prevent a circumstance in which it erroneously proceeds to the next step in the middle of the maintenance operation.

On the maintenance guide screen 201, the guidance information display region 245 described above displays progress in the maintenance of each module and the maintenance operations of the respective modules can be independently controlled by the Next button 246 and Stop button 247.

Figure 7:
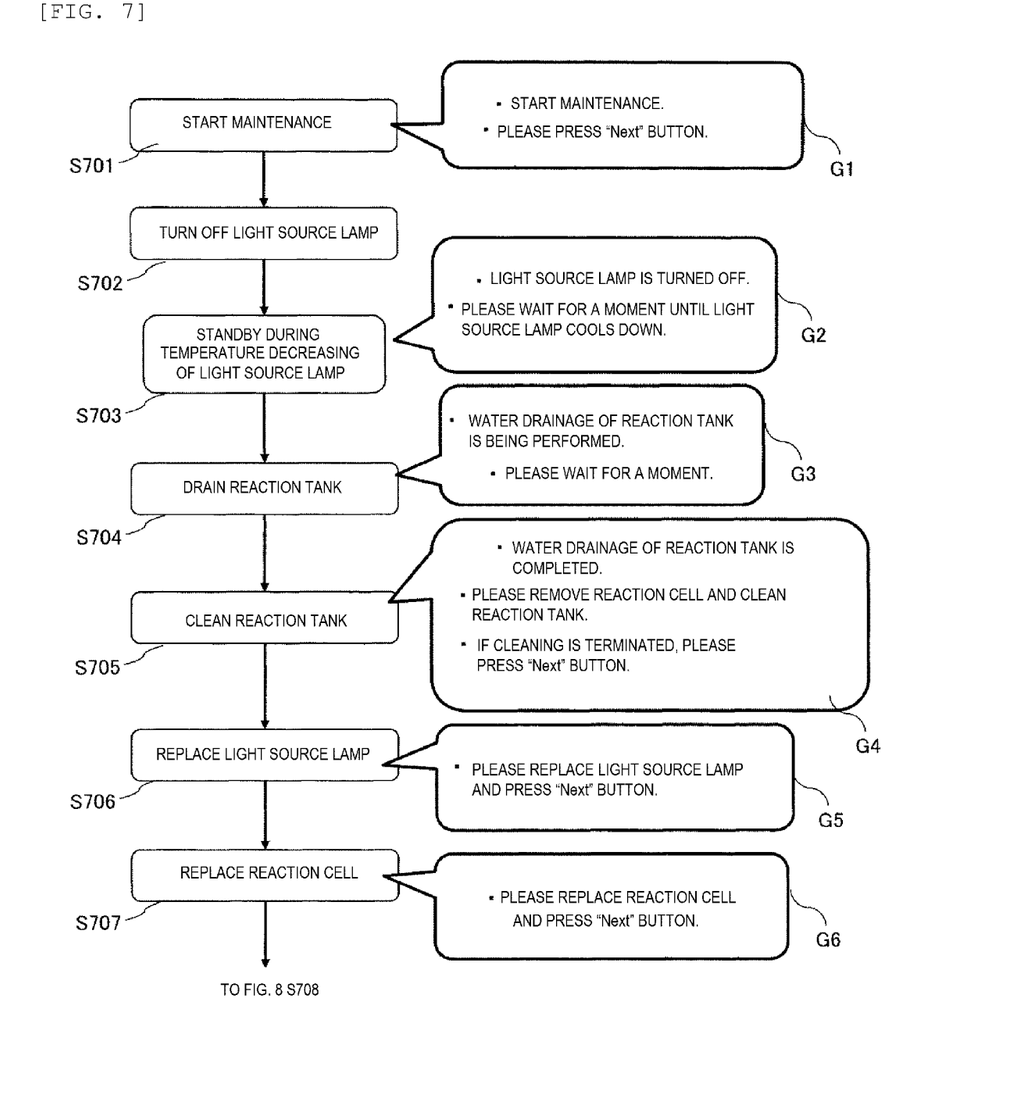
FIG. 7 is a diagram showing a relationship between a flowchart of maintenance operations and message contents on the maintenance guide screen according to the present embodiment.

On the maintenance guide screen 201 shown in FIG. 5, as will be described later with reference to FIGS. 7 and 8, a situation in which some modules, which involve manual operation by an operator, some modules, which are operated by an apparatus and the operator needs to stand by, and other modules are mixedly present in a plurality of modules, is shown.

Specifically, the analysis module 107 is in a step in a state of being on standby where the temperature of the light source lamp decreases (described later in step S703 of FIG. 7), and necessary information is displayed in each of the status display region 243, the remaining time/count information display region 244, and the guidance information display region 245 of the display region 232 for first analysis module that guide maintenance.

In this case, since the temperature of the lamp of the light source is being decreased, it is not possible to proceed to the next step until a predetermined time has elapsed. Therefore, until that time elapses, the Next button 246 is configured to be disabled (cannot be pressed).

On the other hand, the analysis module 207 is in a state where the reaction tank is being cleaned (similar to the state described later in step S704 of FIG. 7), and necessary information is displayed in each of the status display region 243 and the guidance information display region 245 of the display region 230 for second analysis module that guide maintenance.

In this case, since there is no time required for waiting, the time is not displayed in the remaining time/count information display region 244. Since it is possible to proceed to the next step when the manual operation of the operator is completed, the Next button 246 is configured to be valid (so that it can be pressed).

As described above, in the automatic analysis apparatus configured with a plurality of modules, by displaying information necessary for performing and managing maintenance of each module on the same screen, the operator can see at a glance which module is in what progress, how long it will take, and what the next necessary operation is, and thus it is possible to proceed with the operation while grasping the situation all at once.

By operating the buttons displayed on the same screen, operation instructions can be sent independently to the respective modules, and thus there is no need to worry about operation mistakes caused by switching screens when executing maintenance on one module and it is possible to proceed reliably without affecting the operation of the other module.

In the configuration described above, although the configuration for displaying various information on all the modules of the analysis module 107, the sampler module 200, and the analysis module 207 has been described, by providing a selection button (selection region) such as a check box for selecting to display only one of these modules or two or more modules, and a child screen for selection, it is possible to configure so that only the information of the desired module can be confirmed.

In the present embodiment, the guidance is just shown by a text message, but as long as the guidance information display region 245 allows, an image or a moving image may be pasted, and a button for activating voice guidance information can be provided.

Next, a flow of the maintenance guide in the automatic analysis apparatus of the present embodiment will be described with reference to FIGS. 7 and 8. FIGS. 7 and 8 are diagrams showing a relationship between a flowchart of maintenance operations and message contents on the maintenance guide screen.

Here, as an example, a case of performing optical system maintenance consisting of a series of work steps for exchanging the light source lamp and the reaction cell in the analysis module 107, which is a biochemical analysis module, cleaning the reaction tank, supplying circulating water, and stabilizing the temperature during the reaction will be described.

By the operation described above in FIG. 3, when the operator selects the maintenance that he or she wants to perform and instructs the maintenance to be performed, maintenance is started (step S701).

First, in the guidance information display region 245 on the maintenance guide screen 201 shown in FIG. 5, confirmation of the start of maintenance and necessary operations are displayed (G1), and the operator is asked to confirm whether or not the actual maintenance needs to be started. Here, when the operator presses the Next button 246 shown in FIG. 5, the processes at step S702 and subsequent steps are started.

Next, the control unit 114 of the control device 300 turns off the light source lamp with the start of maintenance (step S702). Since the light source lamp generates heat with energization, there is a risk of burns if the operator touches the light source lamp immediately after turning it off. For that reason, it is necessary to wait until the light source lamp cools down.

Next, the control unit 114 of the control device 300 provides a standby time for the temperature decreasing time of the light source lamp (step S703). However, without any guide information here, especially for an operator who is unfamiliar with maintenance, it is not clear what the device is doing during this standby time and how long the operator should wait.

Therefore, at this time, in the guidance information display region 245 of the maintenance guide screen 201 shown in FIG. 5, the matters that the light source lamp has been turned off and that a standby time is required is displayed as a message (G2). According to this, the time required for waiting generally takes about 15 minutes as a whole, and thus specific information on the remaining time is displayed in the remaining time/count information display region 244.

The control unit 114 of the control device 300 automatically proceeds to step S704 when the standby time is completed.

Next, the control unit 114 of the control device 300 unplugs the reaction tank and drains water from the reaction tank (step S704). It usually takes about 10 minutes for all the water in this reaction tank to be drained. Therefore, similarly to the matters described above, the control unit 114 of the control device 300 displays, as a message in the guidance information display region 245 of the maintenance guide screen 201 shown in FIG. 5, that the reaction tank is being drained and that a standby time is required (G3). According to this, specific remaining time information is displayed in the remaining time/count information display region 244.

The control unit 114 of the control device 300 automatically proceeds to step S705 when the standby time elapses and the drainage operation is completed.

Next, the reaction tank is cleaned by the operation of the operator (step S705). For this purpose, the control unit 114 of the control device 300 displays a message, in the guidance information display region 245 of the maintenance guide screen 201 shown in FIG. 5, that the water drainage of the reaction tank is completed, and that prompts the reaction cell to be removed and the reaction cell to be cleaned as necessary operations, and prompts the Next button 246 to be pressed when the operations are terminated (G4).

In this case, the operator performs an operation according to this guidance and presses the Next button to proceed to step S706.

Next, the light source lamp is replaced by the operation of the operator (step S706). For this purpose, the control unit 114 of the control device 300 displays a message, in the guidance information display region 245 of the maintenance guide screen 201 shown in FIG. 5, that prompts the light source lamp to be replaced as a necessary operation and prompts the Next button 246 to be pressed when the operation is terminated (G5).

In this case, the operator performs an operation according to this guidance and presses the Next button to proceed to step S707.

Next, the reaction cell is replaced by the operation of the operator (step S707). For this purpose, the control unit 114 of the control device 300 displays a message, in the guidance information display region 245 of the maintenance guide screen 201 shown in FIG. 5, that prompts the reaction cell to be replaced as a necessary operation and prompts the Next button 246 to be pressed when the operation is terminated (G6).

Figure 8:
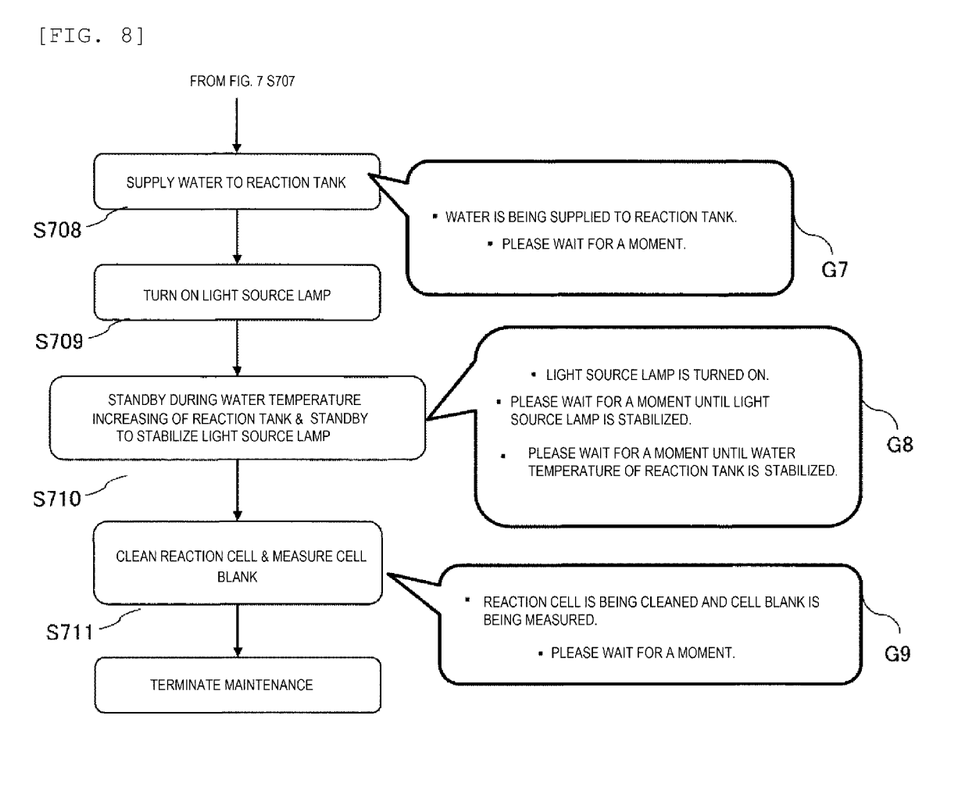
FIG. 8 is a diagram showing a relationship between the flowchart of the maintenance operations and the message contents on the maintenance guide screen according to the present embodiment.

In this case, the operator performs an operation according to this guidance and presses the Next button to proceed to step S708 shown in FIG. 8.

Next, the control unit 114 of the control device 300 plugs the reaction tank and supplies water to the reaction tank (step S708). In this case, the control unit 114 of the control device 300 displays as a message that the water is being supplied to the reaction tank and that the standby time is required (G7). According to this, specific remaining time information is displayed in the remaining time/count information display region 244.

The control unit 114 of the control device 300 automatically proceeds to step S709 when the standby time elapses and the water supply operation is completed.

Next, the control unit 114 of the control device 300 automatically turns on the light source lamp (step S709). Here, since the amount of light of the light source lamp is not stable by simply energizing the light source lamp, the control unit 114 of the control device 300 waits for the elapse of the standby time until the light source lamp is stabilized (step S710). Since the temperature of the water in the reaction tank immediately after water supply is low, it cannot be immediately used for sample measurement. Therefore, it is also necessary to provide a standby time until the temperature increases in the reaction tank.

However, similarly to the matters described above, without any guide information here, especially for an operator who is unfamiliar with maintenance, it is not clear what the device is doing during this standby time and how long the operator should wait. Therefore, the control unit 114 of the control device 300 displays as a message, in the guidance information display region 245 of the maintenance guide screen 201 shown in FIG. 5, that the light source lamp is turned on, that a standby time for stabilization is required, and that a standby time is required for the water temperature in the reaction tank to stabilize (G8). According to this, specific remaining time information is displayed in the remaining time/count information display region 244.

The control unit 114 of the control device 300 automatically proceeds to step S711 when the standby time elapses and the stabilization of the water temperature of the light source lamp and the reaction tank is completed.

Next, the control unit 114 of the control device 300 performs cleaning of the replaced reaction cell and measurement of each cell blank value for making it measurable in the final step of a series of maintenance operations (step S711).

In this case, the control unit 114 of the control device 300 displays as a message, in the guidance information display region 245 of the maintenance guide screen 201 shown in FIG. 5, that the device is performing these operations and that a standby time until the termination is required (G9). When the process of this step is completed, the maintenance is terminated.

Each step from step S701 to step S711 described above is displayed in the status display region 243 on the maintenance guide screen 201 shown in FIG. 5. For example, step S705 is expressed as a status display such as "reaction tank cleaning", and step S710 is expressed as a status display such as "standby during temperature increasing of light source lamp".

Next, the effect of the present embodiment will be described.

The automatic analysis apparatus 100 of the present embodiment described above includes at least one analysis module 107 and 207 that analyzes the sample, the sampler module 200 that holds a plurality of sample containers housing the samples and that supplies the sample containers to the analysis modules 107 and 207, the display unit 116 that displays information on maintenance of the analysis modules 107 and 207 and maintenance of the sampler module 200, and the control unit 114 that controls the operation of the analysis modules 107 and 207 and the operation of the sampler module 200, and that causes the display unit 116 to display information on maintenance, in which the control unit 114 causes the display device 116 to display the maintenance guide screen 201 in which maintenance guidance independent of the analysis modules 107 and 207 and the sampler module 200 is arranged in the same screen.

By doing this, the maintenance action of each module can be executed in parallel without hesitation by following the guidance for each module in the maintenance guide screen 201.

For that reason, even an operator who is unfamiliar with maintenance can easily confirm what kind of operation is necessary for which module and what the current state is without confusion. If the operator is skilled to some extent, he or she can grasp the progress only by confirming the state displayed in the status display region 243 without confirming all the messages displayed in the guidance information display region 245. In this way, labor for maintenance work can be saved as compared with the conventional case.

The analysis modules 107 and 207 and the sampler module 200 each include an in-unit control unit that controls an operation of equipment in each module independently of an operation of another module, and in the maintenance guide screen 201, progress in the maintenance of the respective modules is displayed, and the maintenance operation can be independently controlled, and thus maintenance can be efficiently performed without being affected by the operation such as maintenance of other modules.

Furthermore, the control unit 114 causes the maintenance guide screen 201 to display the status display region 243 that displays a device state of each module, thereby capable of enabling the operator to easily grasp the maintenance progress status and the device state of the module, and to proceed with the maintenance operation more easily and in an easy-to-understand manner.

The control unit 114 causes the maintenance guide screen 201 to display the remaining time/count information display region 244 that displays the remaining time until termination of maintenance of each module to thereby allow the operator to easily grasp how much room is left until the next work, and thus the maintenance work can be carried out more efficiently.

Furthermore, the control unit 114 also causes the maintenance guide screen 201 to display the remaining time/count information display region 244 that displays the number of times of repetitive operations of the maintenance of each module to thereby allow the operator to easily grasp how much room there is before proceeding to the next work, and thus the maintenance work can be carried out more efficiently.

The control unit 114 causes the maintenance guide screen 201 to display the Next button 246 and Stop button 247 in which an operation instruction is performed independently for each module, thereby capable of efficiently performing the maintenance operation of the module without being affected by various operations of the other module.

Furthermore, the control unit 114 provides the guidance for each module in the same arrangement relationship as that of each module when the automatic analysis apparatus 100 is viewed from the position where the operator views the maintenance guide screen 201 to thereby allow the operator who views the maintenance guide screen 201 to grasp which module the guidance is for more intuitively, and thus the maintenance operation can be carried out more easily and in an easy-to-understand manner.

The control unit 114 causes the maintenance guide button 614, which performs transition to the maintenance guide screen 201, to be displayed in the global screen 601 when the global screen 601 is displayed on the display unit 116, thereby capable of providing the operator with a means for making he or she easily proceed to the maintenance guide screen 201.

Furthermore, the control unit 114 causes the maintenance guide button 614, which performs that transitions to the maintenance guide screen 201, to be displayed in the maintenance screen 301 when the maintenance screen 301 is displayed on the display unit 116 and causes the maintenance guide button 404, which performs transition to the maintenance guide screen 201, to be displayed in the overview screen 401 when the overview screen 401 that displays an outline of the automatic analysis apparatus 100 is displayed on the display unit 116, thereby capable of providing a means for making proceed easily to the maintenance guide screen 201.

The control unit 114 causes a selection area to be displayed, the selection region causing only the maintenance guide screen 201 of the module to be displayed among a plurality of modules to be displayed, and causes the maintenance guide screen 201 of the selected module among the plurality of modules to be displayed separately to thereby allow the operator to concentrate on the maintenance operation of the module, and thus the convenience for the operator can be improved.

Furthermore, when it is necessary to notify an operator of a maintenance status at a timing when the maintenance of the module is performed in background and a screen other than the maintenance guide screen 201 is displayed on the display unit 116, the control unit 114 can recommend the operator to proceed to the maintenance guide screen 201 and confirm the operation to be performed next by displaying notification information. Therefore, the operator can smoothly and surely perform the necessary operation without omission.

Such an effect of the present invention is particularly effective when two or more analysis modules are connected to the sampler module.

Even if the configurations of the analysis modules are the same, the progress statuses of maintenance are not necessarily the same. Therefore, even if the configurations are the same, it is possible to contribute to the reduction of the time during which analysis is not possible associated with overall maintenance by making it possible to easily confirm the progress statuses of maintenance of a plurality of modules on the same screen and to instruct and perform a plurality of different maintenances at the same time.

<Others>

The present invention is not limited to the embodiments described above, and various modifications and applications are possible. The embodiments described above have been described in detail in order to explain the present invention in an easy-to-understand manner, and are not necessarily limited to those having all the described configurations.

For example, in the embodiments described above, the configuration in which one sampler module is connected to two analysis modules has been described, but an automatic analysis apparatus including three analysis modules, four analysis modules, and more analysis modules can be adopted.

Even when three or more analysis modules are connected in this way, it is desirable to display the modules in the same arrangement as arrangement (actual device layout) of the respective modules when the automatic analysis apparatus 100 is viewed from the position where the operator views the maintenance guide screen 201.

It is also possible to adopt a device configuration including one analysis module and one sampler module.

In the embodiments described above, although the automatic analysis apparatus using the sample rack 101 capable of being loaded with a plurality of sample containers has been described, it is not always necessary to transport the sample in the sample rack 101, and a configuration in which a sample holder on which only one sample container is loaded is used may be adopted, or the automatic analysis apparatus may have a structure including a sample disk or the like on which a sample is directly placed.

REFERENCE SIGNS LIST

100: automatic analysis apparatus
101: sample rack
101a: emergency sample rack
102: sample rack supply unit
103: sample rack housing unit
104: transport line
105: sample identification device
106: rack rotor
106a, 106b: slot
107, 207: analysis module (analysis unit)
107a, 200a, 207a: in-module control unit
108, 208: sample dispensing mechanism
109, 209: dispensing line
110, 210: sample identification device
112: emergency specimen rack input unit
113: emergency sample rack standby area
114: control unit
115: storage unit
116: display unit (display device)
117: input unit
118, 218: reaction disk
119, 219: reagent disk
120, 220: reagent dispensing mechanism
200: sampler module (transport unit)
201: maintenance guide screen (guide screen)
230: display region for second analysis module
231: display region for sampler module
232: display region for first analysis module
242: module name display region
243: status display region
244: remaining time/count information display region (remaining time information display region, and number of times information display region)
245: guidance information display region
246: Next button (instruction region)
247: Stop button (instruction region)
248, 407, 615: Close button
300: control device
301: maintenance screen
302: maintenance classification display region
303: maintenance detailed information display region
305: maintenance item No.
306: maintenance classification
308: information on each module
309: action information
310: date and time information
401: overview screen
402: layout display region
403: status display region
404: maintenance guide button (transition region)
405: detailed information display region
408: E module (immunity)
409: C module (biochemistry)
410: S module
501: confirmation screen
502: OK button
503: Cancel button
601: global screen
602: power button
603: help button
604: online manual button
605: menu button 606: overview button
607: maintenance button
608: alarm button
609: report button
610: stop button
611: start button
614: maintenance guide button (transition region)

The invention claimed is:

1. An automatic analysis apparatus that analyzes a sample, the automatic analysis apparatus comprising:
at least one analysis unit that analyzes the sample;
a transport unit that holds a plurality of sample containers housing the samples and that supplies the sample containers to the analysis unit;
a display device that displays information on maintenance of the analysis unit and maintenance of the transport unit; and
a control unit that controls an operation of the analysis unit and an operation of the transport unit, and that causes the display device to display information on maintenance, wherein
through a user pressing a maintenance guide button, the control unit causes the display device to display a guide screen in which maintenance guidance of the analysis unit and the transport unit are arranged in the same screen, wherein the maintenance guide button is displayed across multiple screens of the user interface, allowing quick access to the guide screen from any operational state,
wherein the control unit causes the maintenance guide button to be displayed in both a global region and a local region of a maintenance screen when the maintenance screen is displayed on the display device, and
wherein the control unit allows maintenance for any of the units to be controlled independently and performed in parallel.

2. The automatic analysis apparatus according to claim 1, wherein
the analysis unit and the transport unit each include an in-unit control unit that controls an operation of equipment in each unit independently of an operations of another unit, and in the guide screen, progress in the maintenance of the respective units is displayed.

3. The automatic analysis apparatus according to claim 1, wherein
the control unit causes the guide screen to display a status display region that displays a device state of each unit.

4. The automatic analysis apparatus according to claim 1, wherein
the control unit causes the guide screen to display a remaining time information display region that displays remaining time until termination of the maintenance of each unit.

5. The automatic analysis apparatus according to claim 1, wherein
the control unit causes the guide screen to display a number of times information display region that displays the number of repetitive operations of the maintenance of each unit.

6. The automatic analysis apparatus according to claim 2, wherein
the control unit causes the guide screen to display an instruction region in which an operation instruction is performed independently for each unit.

7. The automatic analysis apparatus according to claim 1, wherein
the control unit provides the guidance for each unit in the same arrangement relationship as that of each unit when the automatic analysis apparatus is viewed from a position where an operator views the guide screen.

8. The automatic analysis apparatus according to claim 1, wherein
the control unit causes a transition region, which performs transition to the guide screen, to be displayed in an overview screen when the overview screen that displays an outline of the automatic analysis apparatus is displayed on the display device.

9. The automatic analysis apparatus according to claim 1, wherein
the control unit causes a selection region to be displayed, the selection region causing only a guide screen of the unit to be displayed among a plurality of units to be displayed.

10. The automatic analysis apparatus according to claim 1, wherein
the control unit causes a guide screen of a selected unit among the plurality of units to be displayed separately.

11. The automatic analysis apparatus according to claim 1, wherein
when it is necessary to notify an operator of a maintenance status at a timing when the maintenance of the unit is performed in background and a screen other than the guide screen is displayed on the display device, notification information is displayed.

12. A maintenance guidance method in an automatic analysis apparatus, the automatic analysis apparatus including at least one analysis unit that analyzes a sample, a transport unit that holds a plurality of sample containers housing the samples and that supplies the sample containers to the analysis unit, a display device that displays information on maintenance of the analysis unit and maintenance of the transport unit, and a control unit that controls an operation of the analysis unit and an operation of the transport unit, and that causes the display device to display information on maintenance, the maintenance guidance method in the automatic analysis apparatus comprising:
causing the display device to display a guide screen in which maintenance guidance of the analysis unit and the transport unit is arranged in the same screen through a user pressing a maintenance guide button, wherein the maintenance guide button is displayed across multiple screens of the user interface, allowing quick access to the guide screen from any operational state,
wherein the control unit causes the maintenance guide button to be displayed in both a global region and a local region of a maintenance screen when the maintenance screen is displayed on the display device, and
allowing maintenance for any of the units to be controlled independently and performed in parallel.

* * * * *